United States Patent [19]
Carroll et al.

[11] Patent Number: 5,397,324
[45] Date of Patent: Mar. 14, 1995

[54] SURGICAL STAPLER INSTRUMENT AND METHOD FOR VASCULAR HEMOSTASIS

[76] Inventors: Brendan J. Carroll, 2278 Betty La., Beverly Hills, Calif. 90210; Stewart H. Gleischman, 985 Carmelian St., Los Angeles, Calif. 90049

[21] Appl. No.: 28,886

[22] Filed: Mar. 10, 1993

[51] Int. Cl.$^6$ .......................................... A61B 17/072
[52] U.S. Cl. .................................. 606/139; 606/151; 128/898; 227/19; 227/178; 227/180
[58] Field of Search ................. 606/139, 151; 128/898; 227/176, 178, 175, 180, 181, 19

[56] References Cited

U.S. PATENT DOCUMENTS

| | | | |
|---|---|---|---|
| 4,429,695 | 7/1984 | Green | 227/180 X |
| 4,520,817 | 6/1985 | Green | 227/180 X |
| 4,608,981 | 9/1986 | Rothfuss et al. | 227/19 X |
| 5,014,899 | 5/1991 | Presty et al. | 227/19 X |
| 5,263,629 | 11/1993 | Trumbull et al. | 606/151 X |

Primary Examiner—Rinaldi I. Rada
Attorney, Agent, or Firm—Frederick Gotha

[57] ABSTRACT

An improved surgical stapler instrument and method for enhancing blood vessel hemostasis is set forth where the improvement consists of the use of flexible body-absorbable or non-absorbable pads carried by the stapler cartridge and interposed between the stapler cartridge and the anvil. The flexible pads are captively and releasably held by the stapler cartridge by overhanging arms which are laterally and oppositely spaced from the longitudinal axis of the stapler instrument and sufficiently spaced laterally to permit the anvil to compressively bear against the anvil engagement face of the stapler cartridge. The flexible pads are captively held during the positioning of body-tissue between the anvil and stapler cartridge and released after the staples penetrate through the pad, then the tissue and then formed against the anvil.

35 Claims, 4 Drawing Sheets

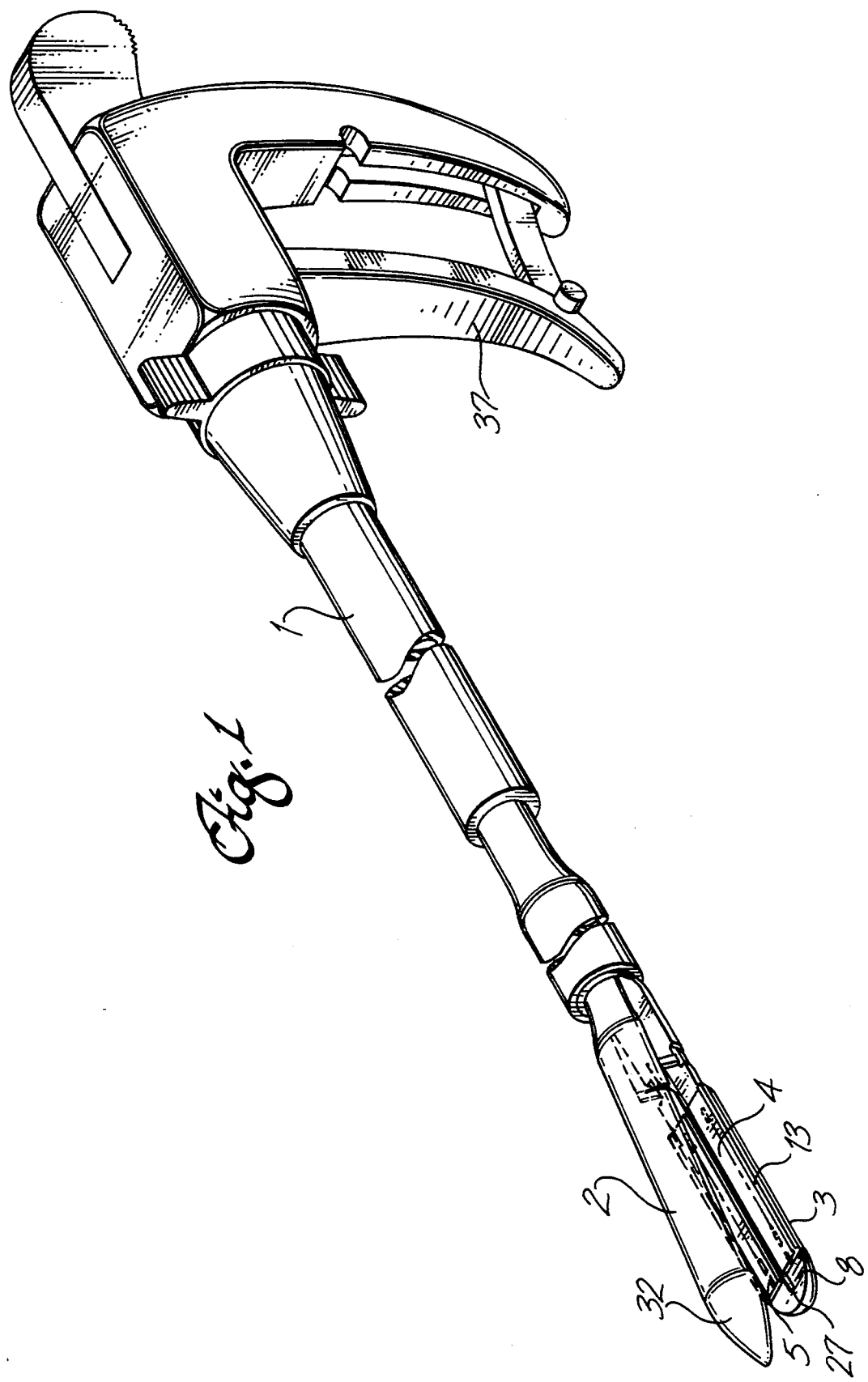

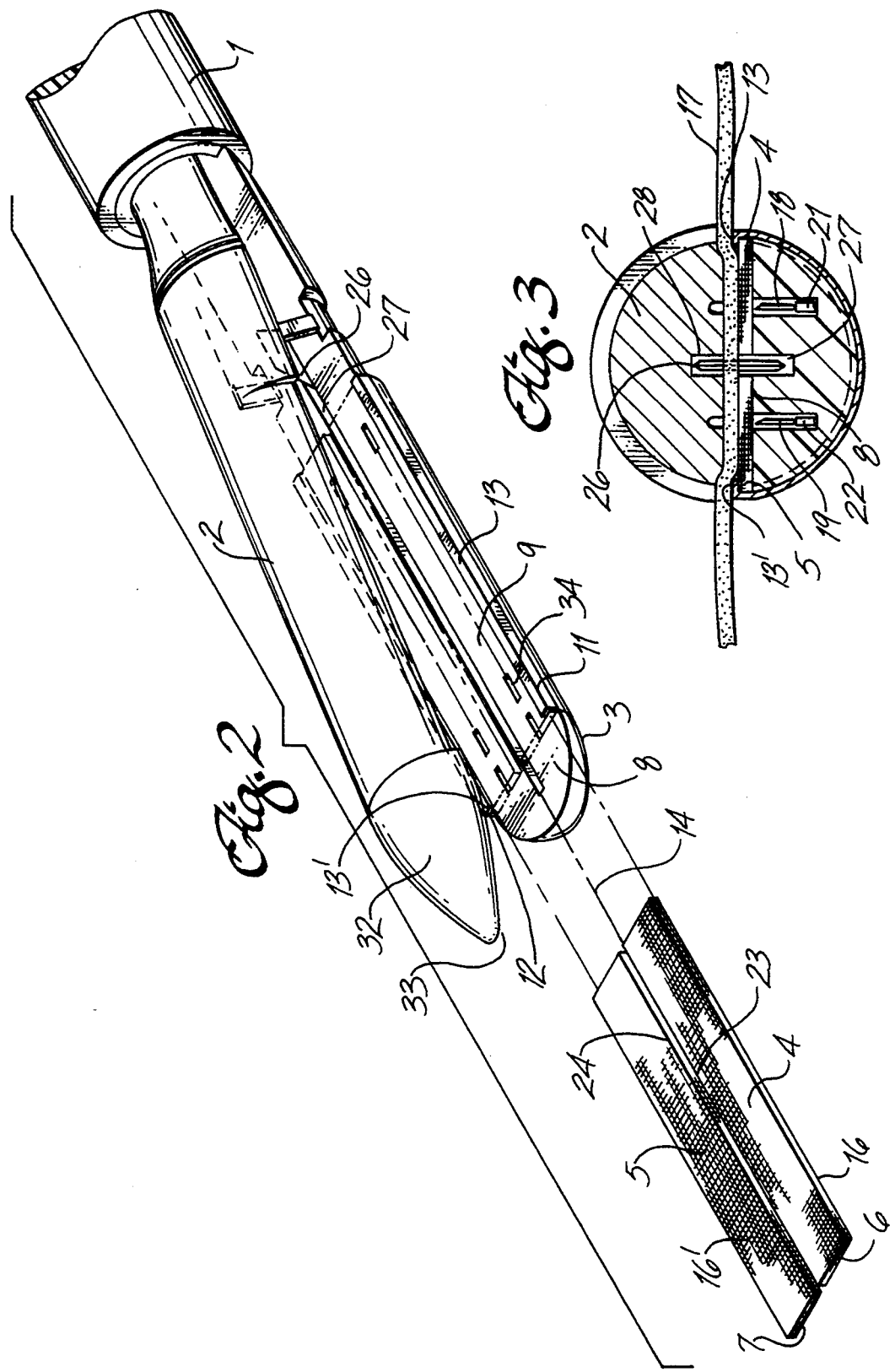

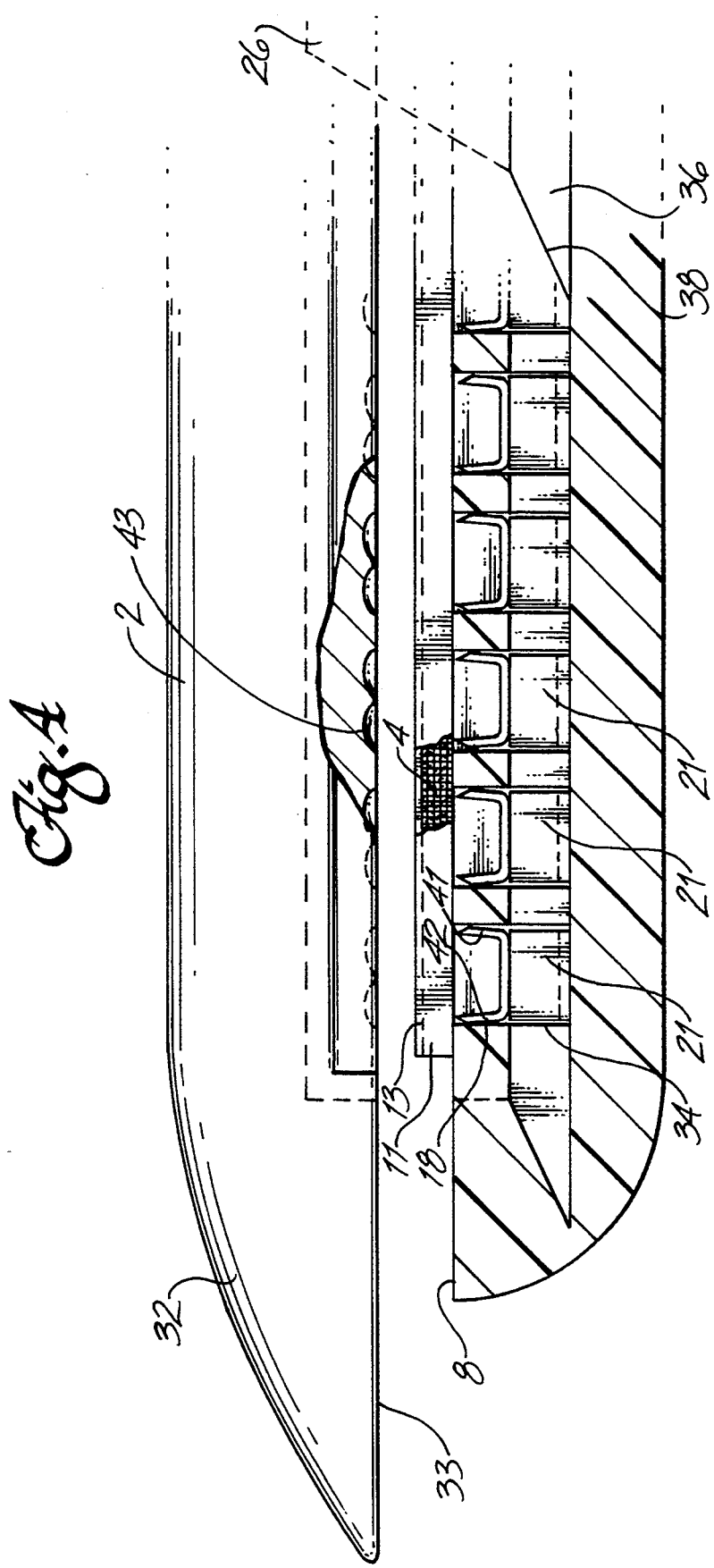

SURGICAL STAPLER INSTRUMENT AND METHOD FOR VASCULAR HEMOSTASIS

FIELD OF THE INVENTION

This invention relates to an improved surgical stapler instrument and method for enhancing hemostasis on the cut ends of blood vessels by securing flexible body absorbable or non-absorbable pads compressively to the ends of the cut blood vessels by linear rows of staples.

BACKGROUND OF THE INVENTION

Staples have traditionally been used in the prior art to replace suturing when joining or anastomosing various body structures such as the bowel or bronchus. Recently, however, stapling devices have been used for ligating and dividing individual blood vessels. Traditionally, to prevent bleeding from the cut ends of the blood vessels, ligatures or vascular clips have been used. By the use of staples, however, individual rows of staple lines are used to prevent bleeding and the staple lines are generally laid perpendicularly to the blood vessel to bracket the cut ends of the blood vessel. Current linear stapler instruments apply rows of staggered staples orthogonally across the ends of the vessels thereby occluding them prior to the division or cutting of the vessel. Unfortunately, bleeding through the rows of staples is a very common problem following application of the staggered staple rows to the blood vessels. This occurs because the blood vessels are elastic and tend to stretch or contact during the application of the stapler lines and bleeding can therefore occur between the individual staples and each row of staples. To reduce such bleeding from the cut ends of blood vessels additional rows of staples have been added to the linear stapling devices of the prior art thereby increasing the number of rows of staples that perpendicularly cross the ends of the vessels. By increasing the number of rows of staples, the size of the stapling gun cartridge head and anvil must also be increased which limits the utility of the stapler instrument particularly in minimally invasive or laparoscopic surgery since access to the operative region requires the gun head to pass through trocars of very small diameter.

The increased acceptance of surgery performed by minimally invasive techniques such as laparoscopic surgery, has resulted in an increased use of linear cutter type staplers to ligate and divide blood vessels. The use of liner cutter type staplers eliminates the need for suturing or knot-tying which is difficult and tedious when performed using minimally invasive techniques. Such techniques require tiny body access incisions and the use of trocars for the insertion of instruments through the trocars in order to reach the operative region in the patient. Knot-tying techniques are time consuming and difficult to master when performing minimally invasive surgery; likewise to achieve hemostasis or to arrest blood vessel bleeding by clipping the individual vessels with metal clips pressed over the ends of the vessels prior to dividing them to achieve hemostasis is an awkward laparoscopic technique. Thus, the use of staggered staple rows orthogonally intersecting the blood vessels to achieve hemostasis is the most desirable technique in the prior art to arrest bleeding when a blood vessel is divided during minimal invasive surgery. However, because of the elasticity of the blood vessels which tend to stretch or contract during the application of the rows of staple lines, unarrested bleeding can occur between the individual staples in each row thereby precluding an effective hemostasis.

SUMMARY OF THE INVENTION

There is, therefore, provided according to the present invention, a surgical vascular stapling device and method of hemostasis which may be used in minimally invasive surgery or in open surgical operation to enhance hemostasis of cut blood vessels.

The present invention is directed to an improved surgical stapler instrument of the type having an anvil member located at the distal end of the instrument forming a first jaw and a stapler cartridge having an anvil engagement face mounted oppositely to the anvil member to form a second jaw. The stapler cartridge and anvil are pivotally connected so that body tissue containing the blood vessel which is to be divided may be positioned between the stapler cartridge and the anvil when the jaws are opened and compressively held between the jaws when the jaws are closed. A cutter member is associated with the anvil member and the stapler cartridge for cutting the blood vessel after a stapler ejector ejects the staples from the cartridge with sufficient force to penetrate through the body tissue and to be formed closed against the anvil. The improvement of this invention comprises a pair of flexible pads which are carried by the stapler cartridge and may be either absorbable or non-absorbable by the body and are interposed between the stapler cartridge and the anvil such that the staples upon ejection from the cartridge will penetrate through the pads before the body tissue. The flexible pads are releasably and captively held in a channel having the shape of a key-way slot which is bounded in part by the anvil engagement face of the stapler cartridge and a pair of overhanging arms having axially extending lips which are laterally spaced apart for holding the pads. The lips of the overhanging arms are sufficiently spaced laterally to permit the anvil member to engage the anvil engagement face of the stapler cartridge. The flexible pads are captively held by the stapler cartridge during the positioning of the pad and during the compressing of the body tissue between the anvil and the stapler cartridge. Thus, when the staples are ejected from the stapler cartridge, they penetrate through the pad and the body tissue and are then formed closed against the anvil. When the jaws are thereafter opened, the adherence of the pads to the body tissue permits the pads to be released from the channel and remain in compressive relationship with the blood vessels to achieve enhanced hemostasis. Thus, a broader segment of the end of the blood vessels after cutting is compressed and controlled through the use of a pad to achieve hemostasis rather than through the use of staples alone which may not arrest the bleeding. The use of a pad also allows control of the blood vessel with less rows of staples thereby allowing for modification of the stapler cartridge and anvil to a smaller cross-sectional size which increases the utility of the stapling device for minimally invasive surgery.

In one embodiment of this invention, the stapling device utilizes a pair of body absorbable or non-absorbable pads which are symmetrically mounted laterally of the cutter member. This allows the cutter member to divide the blood vessel without having to cut the pad. In another embodiment, a single pad is utilized having an axially extending series of individual slots which provide minimal resistance to the cutting blade as it advances axially along the anvil to cut the pad and divide the blood vessel. The non-absorbable pads of this invention may be made of cotton; absorbable pads may be made of materials identified by the trademark "VICRYL", a trademark of Johnson & Johnson, or "DEXON" a trademark of Davis and Geck, or "TEFLON", a trademark of DuPont de Nemours & Co.

BRIEF DESCRIPTION OF THE DRAWINGS

These and other features and advantages will become appreciated as the same become better understood with reference to the following specification, claims and drawings wherein:

FIG. 1 is a perspective view of the improved surgical stapler instrument of this invention.

FIG. 2 is an exploded view in perspective of the distal end of the surgical stapler instrument illustrating the loading of the stapler cartridge with a pair of flexible pads.

FIG. 3 is a cross-sectional view illustrating the clamping of body tissue between the anvil and stapler cartridge before ejection of the staples from the cartridge.

FIG. 4 is a partial cross-sectional view of the distal end of the improved stapler instrument illustrating the individual staples relative to the flexible pad before the staples are ejected from the staple cartridge.

DETAILED DESCRIPTION

Figure 5:
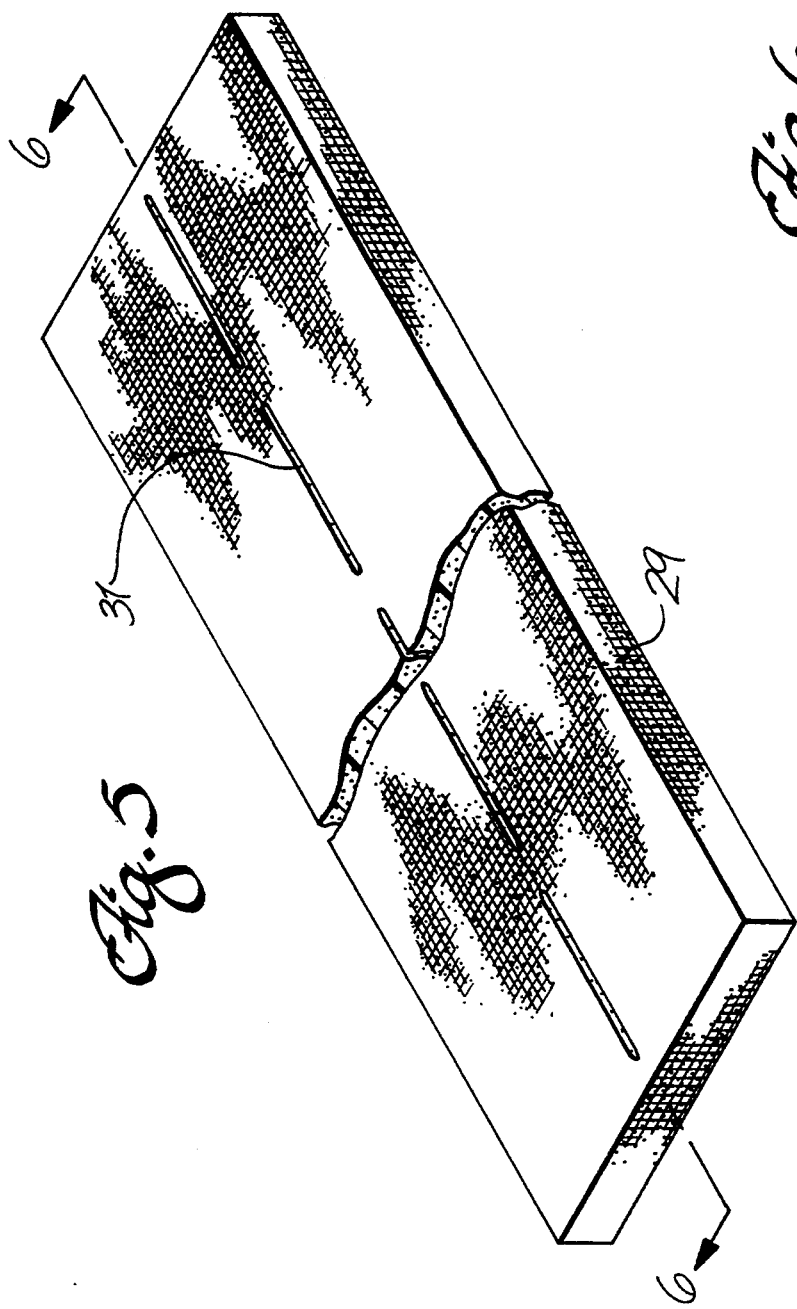
FIG. 5 is a perspective view of an alternative embodiment of the flexible pad of this invention.

Surgical stapling instruments are well known in the prior art and employ a variety of drive mechanisms to push surgical staplers from the stapler cartridge through body tissue and against an opposing anvil where the staplers are formed. Stapling apparatus employing staple drive members are described in U.S. Pat. Nos. 3,490,675, 3,499,591 and 4,978,049, all of which are incorporated by reference herein to illustrate drive mechanism structures which may be utilized to eject staples from a stapler cartridge against an anvil.

In U.S. Pat. No. 4,978,049, a surgical stapling apparatus was shown which included two elongated jaws configured and dimensioned to receive and clamp body tissue between them. One of the jaws carried a stapler cartridge which utilized a plurality of drive members to eject staplers arranged in parallel rows flanking a pusher bar having a cam, while the other jaw included an anvil for forming the staples. The pusher bar of U.S. Pat. No. 4,978,049 traveled longitudinally along the cartridge bearing jaw such that the pusher cam transmitted substantially vertical motion to the plurality of drive members slideably mounted within respectively grooved vertical slots. The drive members drove the staples from the cartridge and through the body tissue with sufficient force to form the staple against the anvil. Parallel rows of staples were driven by the drive member sequentially and were designed so as to resist the torque resulting from staple resistance as the staples were being driven laterally of the stapler instrument longitudinal axis. The present invention is an improvement to the stapler cartridge which permits the cartridge to captively hold body-absorbable or non-absorbable pads through which the staples are driven before being driven through the body tissue. The improved cartridge contains a channel, in the shape of a key-way slot, which is bounded by the anvil engagement face of the stapler cartridge and a pair of overhanging arms which are laterally spaced for captively holding the body-absorbable or non-absorbable pads where the overhanging arms are sufficiently spaced laterally to permit the anvil member to engage the anvil engagement face of the stapler cartridge.

Referring now to FIG. 1, a stapler instrument 1 is shown in perspective having an anvil 2 and the improved stapler cartridge 3 of this invention. By referring to FIG. 2, the anvil 2 and stapler cartridge 3 can be seen in exploded perspective with flexible body-absorbable or non-absorbable pads 4 and 5 also shown in perspective distally of the cartridge 3 before loading. FIG. 2 also illustrates in phantom the flexible pads 4 and 5 after being loaded to stapler cartridge 3 where the undersurfaces 6 and 7 of flexible pads 4 and 5 bear against the anvil engagement face 8 of stapler cartridge 3. As can further be seen in FIG. 2, stapler cartridge 3 has a channel 9 bounded by anvil engagement face 8 and a pair of overhanging arms 11 and 12 which form a keyway slot into which flexible pads 4 and 5 are inserted for captive holding by the stapler cartridge. Flexible pads 4 and 5 are preferably made of body absorbable material commercially known as "TEFLON" which is a registered trademark owned by DuPont de Nemours & Co., or cotton, which is non-absorbable and can be implanted in the body without adverse effects, or other substances which are absorbable by the body such as "VICRYL" which is a registered trademark of Johnson & Johnson or "DEXON" which is a registered trademark of Davis and Geck. To captively hold pads 4 and 5, overhanging arms 11 and 12 are L-shaped and have lips 13 and 13' which are laterally spaced from longitudinal axis 14. Lips 13 and 13' bear against the upper surface of pads 4 and 5 at the lateral extremities of the pads 16 and 16'. Lips 13 and 13' are sufficiently spaced laterally to permit the anvil 2 to apply compression to the anvil engagement face 8 of stapler cartridge 3. This can be more readily seen in FIG. 3 which is a cross-sectional view illustrating body tissue 17 held in compression against pads 4 and 5 by the closure of anvil 2 against anvil engagement face 8 before the staples 18 and 19 have been driven by staple drives 21 and 22 (the staple drive of FIG. 3 is known in the prior art and has been incorporated by reference herein to issued U.S. Patents).

Referring again to FIG. 2, it can be seen that the lateral near edges 23 and 24 of pads 4 and 5 are laterally spaced from each other a sufficient distance to permit cutting knife 26 to pass therebetween as the cutting knife advances axially through cartridge slot 27 and anvil slot 28 to cut the blood vessels contained in the body tissue as the staples are driven through pads 4 and 5 by the plurality of staple drives 21 and 22.

Figure 6:
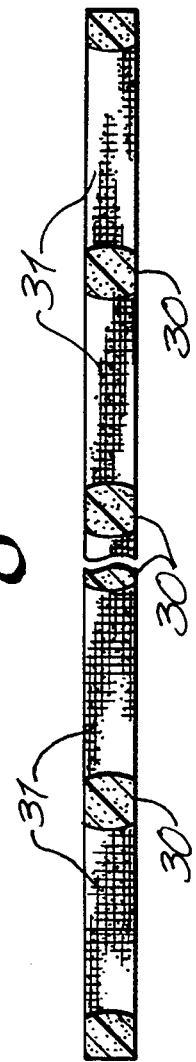
FIG. 6 is a cross-sectional view of FIG. 5 taken along the line 6—6.

Another embodiment of the invention utilizes a flexible pad which is a single pad 29 and has a plurality of longitudinally spaced serrations 31. The serrations 31 are spaced axially along the longitudinal axis of the single pad 29 and are utilized to reduce material resistance to cutting knife 26 as the cutting knife advances axially. As can be seen in FIG. 6, serrations 31 extend vertically through the pad 29 at regular intervals completely through the vertical dimension of the pad such that the cutting knife 26 will cut through cutting regions 30 or voids which offer no resistance to cutting thereby promoting passage of the cutting knife 26 through single pad 29. Single pad 29 may be made of the same material as used in the construction of pads 4 and 5.

As can be seen in FIG. 2, the present invention utilizes two rows of staplers oppositely and laterally spaced from cartridge knife slot 27. A partial cross-section is shown in FIG. 4 illustrating a single row of staples held in stapler cartridge 3 before being driven by the plurality of stapler drives 21. FIG. 4 further illustrates the pad 4 being held by overhanging arm 11 with lip 13 bearing upon pad 4 sufficient to captively hold the pad while the semi-conical probe section 32 of the anvil 2 engages and positions the body tissue between the anvil engagement face 8 of the stapler cartridge 3 and the cartridge engagement face 33 of anvil 2. In the prior art, rows of staples were utilized to perform the same function as suturing when various body structures such as the bowel were joined or anastomosized; rows of staples have recently been used in the prior art to perform hemostasis when ligating and dividing individual blood vessels. The individual staple lines are laid preferably perpendicularly to the blood vessel to prevent bleeding from the cut ends of the blood vessel. The prior art surgical stapler instruments generally placed two to three rows of staples on either side of the stapler cartridge knife slot in order to arrest the bleeding from the cut ends of the blood vessels. Bleeding however, through the rows of staples is a very common problem following application of the staggered staple rows to the blood vessels. Because of the elasticity of the blood vessels which tend to stretch or contract during the application of the staple lines, bleeding can occur between the individual staples in each row. Prior art efforts to reduce bleeding from the cut ends of blood vessels resulted in increasing the number of rows of staples to perpendicularly cross the ends of the vessels to be cut. By adding more rows of staplers, bleeding was more effectively controlled; however, this required increasing the size of the stapler cartridge and anvil and thereby limited the usefulness of the method particularly in performing laparoscopic surgery. The present invention, by utilizing flexible body-absorbable or nonabsorbable pads, seals the gap between the staple rows and compresses a broader portion of the blood vessels being stapled including that portion of the vessel that would not be in direct contact with the staples alone. The present invention therefore, through the use of flexible pads or pledgets allows control of the blood vessel with less rows of staples thereby allowing a stapler cartridge and anvil to be used which are of smaller cross-sectional area and therefore increase the utility of the device particularly in laparoscopic surgery.

Referring again to FIG. 4, the method and operation of the present invention can be described utilizing a stapler driving mechanism used in the prior art. As shown in FIG. 4, a multiplicity of staple drives 21 are housed in the plurality of vertical slots 34 respectively. As in the prior art, the stapler drives are lifted sequentially by cam member 36 as the cam member 36 is advanced axially by an external force applied to the trigger mechanism 37 of the stapler instrument 1. Many types of trigger mechanisms are known in the prior art and are used in surgical stapler instruments to drive the cam 36 axially. When a force is applied to the trigger mechanism, the cam 36 advances and sequentially engages each staple drive 21 which is then ramped upwardly or vertically by ramp 38 of the cam member 36. Stapler drive 21 bears against the staple 18 and thus as the stapler drive ramps up ramp 38, the staple is ejected from the vertical stapler slot 34, through the flexible pad 4, and then through the body tissue 17. Thereafter the staple is formed against the anvil as the vertical arms 41 and 42 of the staple compressively engage the stapler forming recesses 43 located in the cartridge engagement face 33 of anvil 2. Cutting knife 26 is shown in FIG. 4 in hidden lines which extend in a vertical and rearward direction from ramp 38. The location of the cutting knife vertically of the ramp permits the tissue to be cut after the staple is driven by the staple driver through the pad, the body tissue, and then formed against stapler forming recess 43. Cutting, therefore, of the blood vessels does not occur until after the staples have been ejected from the staple cartridge and formed against the anvil.

While an improved surgical stapler device and method to enhance hemostasis has been shown and described, it is to be understood that it is subject to many modifications without departing from the spirit and scope of the claims as recited herein.

What is claimed is:

1. In a surgical stapler instrument for enhancing blood vessel hemostasis of the type having a distal end and a proximal end and a longitudinal axis and an anvil member located at said distal end of said instrument forming a first jaw, a stapler cartridge having an anvil engagement face oppositely mounted to said anvil member at said distal end forming a second jaw and so connected to said anvil member such that body tissue containing said blood vessel may be positioned between said stapler cartridge and said anvil member when said jaws are open and compressively held between said jaws when said jaws are closed, a multiplicity of staples contained within said stapler cartridge, a stapler ejector for ejecting said staples from said stapler cartridge such that said staples penetrate through said body tissue and are formed closed against said anvil member, and a cutter member associated with said anvil member and said stapler cartridge for cutting said blood vessel, wherein the improvement comprises:

a) a pair of flexible pads carried by said stapler cartridge where said flexible pads are sufficiently spaced laterally in fixed spaced relationship to define a longitudinally extending void region between said pads for passage through said void regions by said cutter member during the cutting of said blood vessel without cutting said flexible pads and where said pair of flexible pads are interposed between said stapler cartridge and said anvil member such that said staples upon ejection from said stapler cartridge will penetrate through said flexible pads before said body tissue; and b) holding means carried by said stapler cartridge adjacent said anvil engagement face for captively and releasably holding each said flexible pad such that during the positioning of said body tissue between said anvil member and said stapler cartridge each said flexible pad is captively held by said stapler cartridge in said fixed spaced relationship to permit said cutter member to pass through said void region during the cutting of said blood vessel and thereafter released during the separation of said stapler cartridge from said anvil member after said staples have been formed against said anvil member.

2. The improved stapler device recited in claim 1 wherein said holding means comprises a channel bounded in part by said anvil engagement face of said stapler cartridge and having a pair of overhanging arms laterally and oppositely spaced from said longitudinal axis for captively holding said pads where said overhanging arms are sufficiently spaced laterally to permit said anvil member to compressively bear against said anvil engagement face of said stapler cartridge.

3. The improved stapler device recited in claim 2 wherein said channel forms a key-way slot and each said overhanging arm comprises an axially extending lip member vertically spaced a sufficient distance from said anvil engagement face and substantially parallel thereto for captively holding one of said flexible pads between said lip and said face.

4. The improved stapler device recited in claim 1 wherein said flexible pads are made of cotton.

5. The improved stapler device recited in claim 1 wherein said flexible pads are made of TEFLON.

6. The improved stapler device recited in claim 1 wherein said flexible pads are made of VICRYL.

7. The improved stapler device recited in claim 1 wherein said flexible pads are made of DEXON.

8. In a surgical stapler instrument for enhancing blood vessel hemostasis of the type having a distal end and a proximal end and a longitudinal axis and an anvil member located at said distal end of said instrument forming a first jaw, a stapler cartridge having an anvil engagement face oppositely mounted to said anvil member at said distal end forming a second jaw and so connected to said anvil member such that body tissue containing said blood vessel may be positioned between said stapler cartridge and said anvil member when said jaws are open and compressively held between said jaws when said jaws are closed, a multiplicity of staples contained in said stapler cartridge, a flexible pad having lateral extremities carried by said stapler cartridge and interposed between said stapler cartridge and said anvil member such that said staples upon election from said cartridge will penetrate through said flexible pad before said body tissue, holding means carried by said stapler cartridge adjacent said anvil engagement face for captively and releasably holding said flexible pad such that during the positioning of said body tissue between said anvil member and said stapler cartridge said flexible pad is captively held by said stapler cartridge and released during the separation of said stapler cartridge from said anvil member after said staples have been formed against said anvil member, a stapler ejector for ejecting said staples from said cartridge such that said staples penetrate through said body tissue and are formed against said anvil, and a cutter member associated with said anvil member and said stapler cartridge for cutting said blood vessel, wherein the improvement comprises said flexible pad having a plurality of axial extending serrations spaced intermediate said lateral extremities of said flexible pad defining a series of cutting regions for reducing the cross-sectional area of said flexible pad though which said cutter member advances during the cutting of said blood vessel.

9. The improved stapler device recited in claim 8 wherein said holding means comprises a channel bounded in part by said anvil engagement face of said stapler cartridge and having a pair of overhanging arms laterally and oppositely spaced from said longitudinal axis for captively holding said pad where said overhanging arms are sufficiently spaced laterally to permit said anvil member to compressively bear against said anvil engagement face of said stapler cartridge.

10. The improved stapler device recited in claim 9 wherein said channel forms a key-way slot and each said overhanging arm comprises an axially extending lip member vertically spaced a sufficient distance from said anvil engagement face and substantially parallel thereto for captively holding said flexible pad between said lips and said anvil engagement face.

11. The improved stapler device recited in claim 8 wherein said flexible pad is made of cotton.

12. The improved stapler device recited in claim 8 wherein said flexible pad is made of TEFLON.

13. The improved stapler device recited in claim 8 wherein said flexible pad is made of VICRYL.

14. The improved stapler device recited in claim 8 wherein said flexible pad is made of DEXON.

15. A surgical stapling method utilizing a surgical stapler instrument for enhancing blood vessel hemostasis where said surgical stapler instrument has a distal end and a proximal end, a longitudinal axis and an anvil member located at said distal end of said instrument forming a first jaw, a stapler cartridge having an anvil engagement face oppositely mounted to said anvil member at said distal end forming a second jaw and so connected to said anvil member such that body tissue containing said blood vessel may be positioned between said stapler cartridge and said anvil member when said jaws are opened and compressively held between said taws when said jaws are closed, said stapler cartridge having a multiplicity of staples contained therein, a stapler injector for ejecting said staples from said cartridge such that said staples penetrate through said body tissue and are formed against said anvil and a cutter member associated with said anvil member and said stapler cartridge for cutting said blood vessel, said method comprising the steps of:

a) mounting a pair of flexible pads to said anvil engagement face of said stapler cartridge of said surgical stapler instrument where said flexible pads are sufficiently spaced laterally in fixed spaced relationship to define a longitudinally extending void region between said pads for passage through said void region of said cutter member during the cutting of said blood vessel without cutting said pads;

b) positioning said pair of flexible pads between said body tissue containing said blood vessel and said anvil engagement face of said surgical stapling instrument having at least two parallel rows of staples which can be sequentially ejected from said cartridge and formed against said anvil member of said surgical stapler instrument;

c) fastening said staples to said body tissue such that said rows of staples angularly intersect said blood vessel;

d) passing said cutting member through said longitudinally extending void region between said flexible pads and cutting said body tissue intermediate said rows of staples after said staples are formed against said anvil member sufficiently to divide said blood vessel.

16. In a surgical stapler instrument for enhancing blood vessel hemostasis of the type having a distal end and a proximal end and a longitudinal axis and an anvil member located at said distal end of said instrument forming a first jaw, a stapler cartridge having an anvil engagement face oppositely mounted to said anvil member at said distal end forming a second jaw and so connected to said anvil member such that body tissue containing said blood vessel may be positioned between said stapler cartridge and said anvil member when said jaws are open and compressively held between said jaws when said jaws are closed, a multiplicity of staples contained within said stapler cartridge, a stapler ejector for ejecting said staples from said stapler cartridge such that said staples penetrate through said body tissue and are formed closed against said anvil member, and a cutter member associated with said anvil member and said stapler cartridge for cutting said blood vessel, wherein the improvement comprises:
 a) a pair of flexible pads carried by said stapler cartridge where said stapler pads are sufficiently spaced laterally in fixed spaced relationship to define a longitudinally extending void region between said pads for passage through said void region of said cutter member during the cutting of said blood vessel without cutting said pads, and where said flexible pads are interposed between said stapler cartridge and said anvil member such that said staples upon ejection from said stapler cartridge will penetrate through said flexible pads before said body tissue; and
 b) holding means carried by said stapler cartridge adjacent said anvil engagement face for slideably and releasably holding each said flexible pad such that during the positioning of said body tissue between said anvil member and said stapler cartridge each said flexible pad is captively held by said stapler cartridge in said fixed space relationship to permit said cutter member to pass through said void region during the cutting of said blood vessel and slideably released during the separation of said stapler cartridge from said anvil member after said staples have been formed against said anvil member.

17. The improved stapler device recited in claim 16 wherein said holding means comprises a channel bounded in part by said anvil engagement face of said stapler cartridge and having a pair of overhanging arms laterally and oppositely spaced from said longitudinal axis for captively holding said pads where said overhanging arms are sufficiently spaced laterally to permit said anvil member to compressively bear against said anvil engagement face of said stapler cartridge.

18. The improved stapler device recited in claim 17 wherein said channel forms a key-way slot and each said overhanging arm comprises an axially extending lip member vertically spaced a sufficient distance from said anvil engagement face and substantially parallel thereto for captively holding one of said flexible pads between said lip and said face.

19. The improved stapler device recited in claim 16 wherein said flexible pads are made of cotton.

20. The improved stapler device recited in claim 16 wherein said flexible pads are made of TEFLON.

21. The improved stapler device recited in claim 16 wherein said flexible pads are made of VICRYL.

22. The improved stapler device recited in claim 16 wherein said flexible pads are made of DEXON.

23. In a surgical stapler instrument for enhancing blood vessel hemostasis of the type having a distal end and a proximal end and a longitudinal axis and an anvil member located at said distal end of said instrument forming a first jaw, a stapler cartridge having an anvil engagement face oppositely mounted to said anvil member at said distal end forming a second jaw and so connected to said anvil member such that body tissue containing said blood vessel may be positioned between said stapler cartridge and said anvil member when said jaws are open and compressively held between said jaws when said jaws are closed, a multiplicity of staples contained within said stapler cartridge, a stapler ejector for electing said staples from said stapler cartridge such that said staples penetrate through said body tissue and are formed closed against said anvil, and a cutter member associated with said anvil member and said stapler cartridge for cutting said blood vessel, wherein the improvement comprises:
 a) a pair of flexible pads carried by said stapler cartridge and interposed between said stapler cartridge and said anvil member such that said staples upon ejection from said stapler cartridge will penetrate through said pads before said body tissue; and
 b) holding means carried by said stapler cartridge adjacent said anvil engagement face for captively and releasably holding each said flexible pad such that during the positioning of said body tissue between said anvil member and said stapler cartridge each said flexible pad is captively held by said stapler cartridge and released during the separation of said stapler cartridge from said anvil member after said staples have been formed against said anvil member, said holding means comprising a channel bounded in part by said anvil engagement face of said stapler cartridge and having a pair of overhanging arms laterally and oppositely spaced from said longitudinal axis for captively holding said pads where said overhanging arms are sufficiently spaced laterally to permit said anvil member to compressibly bear against said anvil engagement face of said stapler cartridge.

24. The improved stapler device recited in claim 23 wherein said channel forms a key-way slot and each said overhanging arm comprises an axially extending lip member vertically spaced a sufficient distance from said anvil engagement face and substantially parallel thereto for captively holding one of said flexible pads between said lip and said face.

25. The improved stapler device recited in claim 23 wherein said flexible pads are made of cotton.

26. The improved stapler device recited in claim 23 wherein said flexible pads are made of TEFLON.

27. The improved stapler device recited in claim 23 wherein said flexible pads are made of VICRYL.

28. The improved stapler device recited in claim 23 wherein said flexible pads are made of DEXON.

29. In a surgical stapler instrument for enhancing blood vessel hemostasis of the type having a distal end and a proximal end and a longitudinal axis and an anvil member located at said distal end of said instrument forming a first jaw, a stapler cartridge having an anvil engagement face oppositely mounted to said anvil member at said distal end forming a second jaw and so connected to said anvil member such that body tissue containing said blood vessel may be positioned between said stapler cartridge and said anvil member when said jaws are open and compressively held between said jaws when said jaws are closed, a multiplicity of staples contained in said stapler cartridge, a stapler ejector for ejecting said staples from said cartridge such that said staples penetrate through said body tissue and are formed against said anvil member, and a cutter member associated with said anvil member and said stapler cartridge for cutting said blood vessel, wherein the improvement comprises:
 a) a flexible pad having lateral extremities carried by said stapler cartridge and interposed between said stapler cartridge and said anvil member such that said staples upon ejection from said cartridge will penetrate through said flexible pad before said body tissue; and b) holding means carried by said stapler cartridge adjacent said anvil engagement face for captively and releasably holding said flexible pad such that during the positioning of said body tissue between said anvil member and said stapler cartridge said flexible pad is captively held by said stapler cartridge and released during the separation of said stapler cartridge from said anvil member after said staples have been formed against said anvil member, and where said holding means comprises a channel bounded in part by said anvil engagement face of said stapler cartridge and having a pair of overhanging arms laterally and oppositely spaced from said longitudinal axis for captively holding said pad where said overhanging arms are sufficiently spaced laterally to permit said anvil member to compressibly bear against said anvil engagement face of said stapler cartridge.

30. The improved stapler device recited in claim 29 wherein said channel forms a key-way slot and each said overhanging arm comprises an axially extending lip member vertically spaced a sufficient distance from said anvil engagement face and substantially parallel thereto for captively holding said flexible pad between said lips and said anvil engagement face.

31. The improved stapler device recited in claim 29 wherein said flexible pad further comprises a plurality of axially extending serrations spaced intermediate said lateral extremities of said flexible pad defining a series of cutting regions for reducing the cross-sectional area of said flexible pad through which said cutter member advances during the cutting of said body tissue.

32. The improved stapler device recited in claim 30 wherein said flexible pad is made of cotton.

33. The improved stapler device recited in claim 30 wherein said flexible pad is made of TEFLON.

34. The improved stapler device recited in claim 30 wherein said flexible pad is made of VICRYL.

35. The improved stapler device recited in claim 30 wherein said flexible pad is made of DEXON.

* * * * *